United States Patent
Soerens et al.

(10) Patent No.: US 8,506,755 B2
(45) Date of Patent: Aug. 13, 2013

(54) CREPED TISSUE PRODUCT WITH ENHANCED RETENTION CAPACITY

(75) Inventors: Dave Allen Soerens, Neenah, WI (US); Cathleen Mae Uttecht, Menasha, WI (US); Cynthia Suzanne Krueger, Oshkosh, WI (US)

(73) Assignee: Kimberly-Clark Worldwide, Inc, Neenah, WI (US)

( * ) Notice: Subject to any disclaimer, the term of this patent is extended or adjusted under 35 U.S.C. 154(b) by 331 days.

(21) Appl. No.: 12/980,048

(22) Filed: Dec. 28, 2010

(65) Prior Publication Data
US 2012/0165775 A1   Jun. 28, 2012

(51) Int. Cl.
   D21H 27/40   (2006.01)
   D21H 19/74   (2006.01)
   D21H 21/22   (2006.01)
   D21H 23/56   (2006.01)
   B31F 1/14    (2006.01)

(52) U.S. Cl.
   USPC ........ 162/112; 162/136; 162/168.7; 162/169; 162/177; 162/184; 264/283

(58) Field of Classification Search
   USPC .......... 162/109–113, 123, 124, 127, 158, 162/168.1, 168.3, 175–177, 183, 184, 168.7, 162/169; 604/374, 375; 264/282, 283
   See application file for complete search history.

(56) References Cited

U.S. PATENT DOCUMENTS

| | | | |
|---|---|---|---|
| 4,256,877 A * | 3/1981 | Karlsson et al. | 536/59 |
| 4,500,585 A * | 2/1985 | Erickson | 428/152 |
| 5,865,950 A | 2/1999 | Vinson et al. | |
| 6,150,002 A * | 11/2000 | Varona | 428/99 |
| 6,737,491 B2 | 5/2004 | Soerens et al. | |
| 6,772,443 B2 | 8/2004 | Soerens et al. | |
| 6,808,801 B2 | 10/2004 | George et al. | |
| 6,822,135 B2 | 11/2004 | Soerens et al. | |
| 6,849,685 B2 | 2/2005 | Soerens et al. | |
| 6,887,961 B2 | 5/2005 | Soerens et al. | |
| 6,964,803 B2 | 11/2005 | Krautkramer et al. | |
| 6,984,419 B2 * | 1/2006 | Anderson et al. | 427/385.5 |
| 7,115,321 B2 | 10/2006 | Soerens et al. | |
| 7,138,560 B2 | 11/2006 | Przepasniak et al. | |
| 7,205,259 B2 | 4/2007 | Soerens | |
| 7,294,591 B2 | 11/2007 | Soerens et al. | |
| 7,312,286 B2 | 12/2007 | Lang et al. | |
| 7,335,713 B2 | 2/2008 | Lang et al. | |
| 7,619,131 B2 | 11/2009 | Soerens et al. | |
| 2007/0137808 A1 | 6/2007 | Lostocco et al. | |
| 2007/0137810 A1 | 6/2007 | Dyer et al. | |
| 2008/0128101 A1 * | 6/2008 | Furman et al. | 162/158 |
| 2010/0155004 A1 | 6/2010 | Soerens et al. | |

* cited by examiner

*Primary Examiner* — Eric Hug
(74) *Attorney, Agent, or Firm* — Michael J. Sullivan

(57) ABSTRACT

An absorbent composite material may be manufactured by applying a flexible absorbent binder polymer (FAB), also referred to herein as a flexible superabsorbent, during the creping step of conventional tissue manufacturing. As such, the costly process of applying FAB to a substrate by spraying or printing followed by drying may be eliminated. The creping step has the additional advantage of improving the flexibility and softness of the FAB treated fibrous web.

12 Claims, 3 Drawing Sheets

CREPED TISSUE PRODUCT WITH ENHANCED RETENTION CAPACITY

FIELD OF THE INVENTION

This disclosure relates generally to a creped tissue product comprising a flexible absorbent binder and a water-soluble film forming polymer. By applying a flexible absorbent binder onto the tissue product through the creping process, the flexible absorbent binder is localized at the surface of the fibrous web creating webs having improved absorbency characteristics compared to webs prepared using traditional creping additives and comparable to webs prepared by spraying or printing a superabsorbent polymer onto the web.

BACKGROUND

Flexible superabsorbents are known in the art. Such superabsorbents provide the advantage of being highly absorbent, yet flexible enough to be incorporated into absorbent articles, particularly thin absorbent articles such as pantiliners, that require a high degree of bending. Absorbent articles comprising flexible superabsorbents however are generally manufactured by printing or spraying the nascent superabsorbent onto a nonwoven composite followed by drying. This process not only requires additional equipment compared to the manufacture of traditional absorbent articles, but is also more costly and slower. Also, while the use of flexible superabsorbents results in absorbent articles that are less stiff than similar articles containing traditional superabsorbent materials, the articles may still have stiffness levels that exceed those desired by consumers.

Therefore, there is a need in the art for improved absorbent composites comprising flexible superabsorbents and absorbent articles incorporating the same. One desire is to make absorbent articles thinner. Another desire is to make absorbent articles more flexible. Yet another desire is to improve or maintain the absorbent intake and/or the absorbent capacity of such articles. Overarching all of these desires is the desire to reduce the cost of manufacturing and to use existing manufacturing equipment and processes.

SUMMARY

It has now been surprisingly discovered that an absorbent composite material may be manufactured by applying a flexible absorbent binder polymer (FAB), also referred to herein as a flexible superabsorbent, during the creping step of conventional tissue manufacturing. As such, the costly process of applying FAB to a substrate by spraying or printing followed by drying has been eliminated. The creping step has the additional advantage of improving the flexibility and softness of the FAB treated fibrous web. Furthermore, the creping step effectively localizes the flexible superabsorbent at the surface of the fibrous web creating webs having absorbency characteristics that are better than webs prepared using traditional creping additives and comparable to webs prepared by spraying or printing FAB onto the web.

Accordingly, in one aspect the present disclosure a creped tissue product comprising a creped tissue web having a first side and a second side; and a creping additive composition disposed on at least the first side of the creped tissue web, the additive composition comprising a flexible superabsorbent and a film forming component.

In other aspects the present disclosure provides a creped tissue web comprising a tissue web having a first side and a second side, the tissue web having been creped from a drum dryer to which a creping additive composition has been applied, the creping additive comprising a flexible superabsorbent and a film forming component.

In still other aspects the present disclosure provides an absorbent article comprising a backing layer and an absorbent layer; wherein the absorbent layer is positioned adjacent the backing layer; wherein the absorbent layer comprises a creped tissue sheet having a first side and a second side; and a creping additive composition disposed on at least the first side of the creped tissue sheet, the creping additive composition comprising a flexible superabsorbent and a film forming component.

In yet other aspect the present disclosure provides a process for producing a creped sheet product comprising applying an additive composition comprising a flexible superabsorbent and a film forming component to a moving creping surface; pressing a base sheet against the creping surface after the additive composition has been applied, the additive composition adhering the base sheet to the creping surface; and removing the base sheet from the creping surface with a creping blade, wherein the base sheet comprises, by weight, from about 0.1% to about 3% additive composition.

Other features and aspects of the present disclosure are discussed in greater detail below.

DETAILED DESCRIPTION

Figure 1:
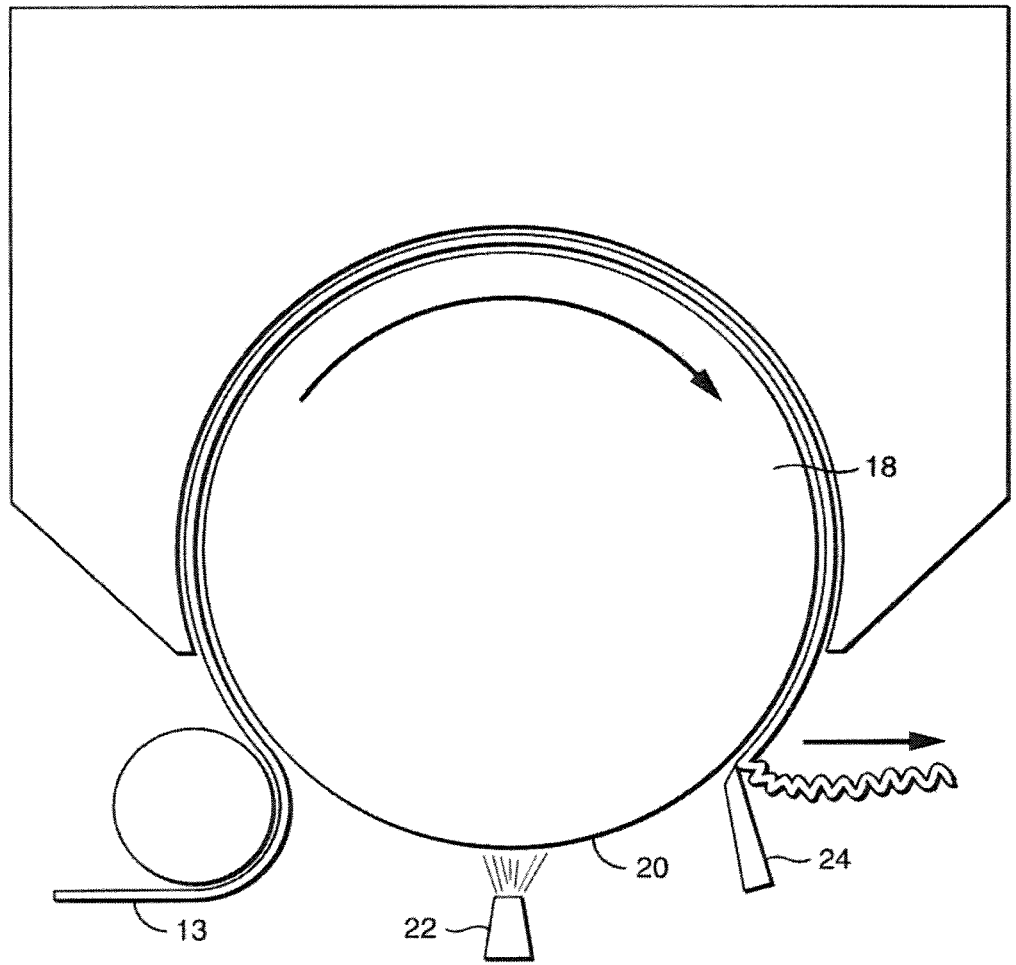
FIG. 1 is a schematic diagram of one aspect of a Yankee dryer used to dry the fibrous web of the present disclosure.

To transfer a creping adhesive onto the tissue web requires creping adhesives having good film forming capability and low cohesive strength. A well formed film with low cohesive strength ensures that failure at the creping blade occurs within the adhesive layer, thereby depositing a portion of the adhesive layer onto the tissue web. Flexible absorbent binders (FAB), although having improved flexibility compared to traditional superabsorbent polymers, cross-link and become brittle when exposed to the high heat of the creping surface, causing increased adhesion to the creping surface and failure outside of the adhesive layer. The result is poor deposition of FAB onto the web surface, decreased creping blade life and poor runability. Thus, to enable the deposition of FAB onto the web surface using conventional creping techniques, the creping additive preferably includes a film forming component. The creping additive may further comprise a modifier component, which may aid in film formation or provide other functional benefits such as improved absorbency.

Accordingly, in general, the present disclosure is directed to a creped tissue product comprising a tissue web that has been creped from a drum dryer to which a creping additive composition comprising an FAB and a water-soluble film forming polymer has been applied. The resulting creped tissue product has an increased retention capacity relative to conventionally creped tissue products, while retaining or improving manufacturing efficiency. In some aspects, a water-soluble modifier component may also be applied to the drum dryer to provide additional benefits and enhanced sheet properties.

In a particularly preferred embodiment the creping additive composition comprises the reaction product of at least 15% by mass monoethylenically unsaturated monomer selected from carboxylic acid, carboxylic acid salts, sulphonic acid, sulphonic acid salts, phosphoric acid, and phosphoric acid salts; a plasticizer; an acrylate or methacrylate ester that contains an alkoxysilane functionality; a chain transfer agent; a transition metal salt; an initiator system; and a neutralizing agent, as the FAB component. Preferably when the FAB component is placed on a substrate and crosslinked, the FAB component forms a superabsorbent layer on the substrate, or may be impregnated into the substrate. In general, the term "superabsorbent materials" refers to water-swellable, water-insoluble organic or inorganic materials capable, under the most favorable conditions, of absorbing at least about 10 times their weight, or at least about 15 times their weight, or at least about 25 times their weight in an aqueous solution containing 0.9 weight percent sodium chloride. In contrast, "absorbent materials" are capable, under the most favorable conditions, of absorbing at least 5 times their weight of an aqueous solution containing 0.9 weight percent sodium chloride. Preferably the formation of a superabsorbent layer on the substrate results in the substrate having an absorbency greater than 5 g/g, such as up to about 7 g/g of the absorbent composite, or about 5.5 g/g to about 6.5 g/g of the absorbent composite, as measured by the Retention Capacity Test.

Referring now to FIG. 1, the additive composition of the present disclosure is applied directly onto the dryer surface 20 (e.g., a Yankee dryer) using a spray boom 22. A general description of the creping process is disclosed, for example, in U.S. Pat. No. 7,820,010, which is incorporated herein by reference in a manner that is consistent herewith. The fibrous web 13 is adhered to the surface of the Yankee dryer when it is pressed into contact with the composition. The fibrous web and the composition are subsequently scraped off of the dryer surface by a creping blade 24.

The additive composition comprises a composition of a flexible absorbent binder (FAB) polymer, which may also be referred to as a flexible superabsorbent polymer. The flexible superabsorbent polymer preferably includes a monoethylenically unsaturated polymer, such as carboxylic acid, sulphonic acid, or phosphoric acid, or salts thereof, and an acrylate or methacrylate ester that contains an alkoxysilane functionality, or a monomer capable of co-polymerization with a compound containing a trialkoxysilane functional group and subsequent reaction with water to form a silanol group wherein the flexible superabsorbent binder polymer composition has a residual monoethylenically unsaturated monomer of less than about 1000 ppm. More specifically, the FAB composition is the reaction product of at least 15% by mass monoethylenically unsaturated carboxylic, sulphonic or phosphoric acid or salts thereof, an acrylate or methacrylate ester that contains an alkoxysilane functionality which, upon exposure to water, forms a silanol functional group which condenses to form a crosslinked polymer, a copolymerizable hydrophilic glycol containing ester monomer; and/or, a plasticizer. Suitable monomers that may be included to make a suitable superabsorbent polymer solution include carboxyl group-containing monomers: for example monoethylenically unsaturated mono- or poly-carboxylic acids, such as (meth)acrylic acid (meaning acrylic acid or methacrylic acid; similar notations are used hereinafter), maleic acid, fumaric acid, crotonic acid, sorbic acid, itaconic acid, and cinnamic acid; carboxylic acid anhydride group-containing monomers: for example monoethylenically unsaturated polycarboxylic acid anhydrides (such as maleic anhydride); carboxylic acid salt-containing monomers: for example water-soluble salts (alkali metal salts, ammonium salts, amine salts, and the like) of monoethylenically unsaturated mono- or poly-carboxylic acids (such as sodium(meth)acrylate, trimethylamine(meth)acrylate, triethanolamine(meth)acrylate), sodium maleate, methylamine maleate; sulfonic acid group-containing monomers: for example aliphatic or aromatic vinyl sulfonic acids (such as vinylsulfonic acid, allyl sulfonic acid, vinyltoluenesulfonic acid, styrene sulfonic acid), (meth)acrylic sulfonic acids (such as sulfopropyl(meth)acrylate, 2-hydroxy-3-(meth) acryloxy propyl sulfonic acid); sulfonic acid salt group-containing monomers: for example alkali metal salts, ammonium salts, amine salts of sulfonic acid group containing monomers as mentioned above; and/or amide group-containing monomers: vinylformamide, (meth)acrylamide, N-alkyl(meth) acrylamides (such as N-methylacrylamide, N-hexylacrylamide), N,N-dialkyl(meth)acryl amides (such as N,N-dimethylacrylamide, N,N-di-n-propylacrylamide), N-hydroxyalkyl(meth) acrylamides [such as N-methylol (meth)acrylamide, N-hydroxyethyl(meth)acrylamide], N,N-dihydroxyalkyl(meth)acrylamides [such as N,N-dihydroxyethyl(meth)acrylamide], vinyl lactams (such as N-vinylpyrrolidone).

Suitably, the amount of monoethylenically unsaturated carboxylic, sulphonic or phosphoric acid or salts thereof relative to the weight of the flexible superabsorbent binder polymer composition may range from about 15% to about 99.9% by weight. In some aspects, the levels of monoethylenically unsaturated carboxylic, sulphonic or phosphoric acid or salts thereof may be between about 25% and about 99.9% by weight of the flexible superabsorbent binder polymer composition, such as between about 25% and about 90% by weight of the flexible superabsorbent binder polymer composition, or between about 30% and about 80% by weight of the flexible superabsorbent binder polymer composition; or between about 50% and about 70% by weight of the flexible superabsorbent binder polymer composition for some intended uses. Suitable FAB polymers and methods of making the same are disclosed in U.S. Pat. Nos. 7,312,286 and 7,335,713, both of which are incorporated herein by reference in a manner consistent with the present disclosure.

The FAB component can be present in the additive composition in any operative amount and will vary based on the chemical component selected, as well as on the end properties that are desired. For example, the FAB component can be present in the additive composition in an amount of about 10-90 wt %, such as 20-80 wt % or 30-70 wt % based on the total weight of the additive composition, to provide improved benefits.

In a preferred embodiment the additive composition further comprises at least one film forming component. The film forming component contained within the additive composition may vary depending upon the particular application and the desired result. Suitable film forming components include, for example, cellulose ethers and esters. Other suitable film forming components include polysaccharides of sufficient chain length to form films such as, but not limited to, pullulan and pectin. The film forming polymer can also contain additional monoethylenically unsaturated monomers that do not bear a pendant acid group, but are copolymerizable with monomers bearing acid groups. Such compounds include, for example, the monoacrylic esters and monomethacrylic esters of polyethylene glycol or polypropylene glycol, the molar masses (Mn) of the polyalkylene glycols being up to about 2,000.

In one particular aspect the film forming component is water-soluble, for example a hydroxypropyl starch, such as the hydroxypropyl starch sold by Chemstar, Minneapolis, Minn. under the brand name GLUCOSOL 800. Other suitable water-soluble film forming components may include, for example, is a hydroxypropyl cellulose (HPC), sold under the brand name of KLUCEL, methyl cellulose (MC), sold under the brand name of BENECEL and hydroxyethyl cellulose sold by under the brand name of NATROSOL, all of which are commercially available from Ashland, Inc., Covington, Ky. The film forming component can be present in the additive composition in any operative amount and will vary based on the chemical component selected, as well as on the end properties that are desired. For example, in the exemplary case of GLUCOSOL 800, the film forming component can be present in the additive composition in an amount of about 10-90 wt %, such as 20-80 wt % or 30-70 wt % based on the total weight of the additive composition, to provide improved benefits. Any of these chemistries, once diluted in water, are disposed onto a Yankee dryer surface with a spray boom 22 to ultimately transfer to the web surface.

In some aspects, the film forming component is dissolved into a 1 wt % aqueous solution, and diluted further as required to provide the desired dosage to be delivered to the drying surface. Addition levels are generally measured as the amount of additive per unit area of drying surface, for example, $mg/m^2$ of dryer surface. The dosage is estimated based on the volume of film forming solution multiplied by the film forming concentration and divided by the square meters of tissue treated per unit time.

In addition to a water-soluble film forming component, the additive composition may include a modifier component. The modifier component is used, among other things, to adjust adhesion of the web to a paper drying surface. The modifier component can also improve paper machine cleanliness (e.g., the paper machine dryer surface and paper machine felts or fabrics). In some aspects, the modifier component is water-soluble, for example, Carbowax PEG 8000 (Dow Chemical, Midland, Mich.). The modifier component can be present in the additive composition in any operative amount and will vary based on the chemical component selected, as well as on the end properties that are desired. For example, in the exemplary case of Carbowax PEG 8000, the modifier component can be present in the additive composition in an amount of about 1-60 wt %, or at least about 1 wt %, such as at least about 5 wt %, or least about 10 wt %, or up to about 30 wt %, such as up to about 40 wt % or up to about 50 wt %, or more, based on the total weight of the additive composition, to provide improved benefits.

Examples of other suitable modifier components include ethylene oxide-propylene oxide block copolymers. The modifier components of the present disclosure may have an average molecular weight that varies depending on the ultimate use of the polymer. Preferably, the water-soluble modifier components of the present disclosure have a weight average molecular weight ranging from about 5,000 to about 100,000 grams per mol. More specifically, the adhesive components of the present disclosure have a weight average molecular weight ranging from about 6,000 to about 100,000 grams per mol, or, more specifically still, from about 8,000 to about 50,000 grams per mol.

In some aspects, the additive composition can be diluted prior to application. The pH of the aqueous solution is generally less than about 12, such as from about 5 to about 9, and preferably about 6 to about 8. In this aspect, the additive composition can be diluted to between 0.20 wt % to 10 wt %, desirably to between 4 to 7 wt %.

In one embodiment, the additive composition may be applied topically to the web during a creping process. For instance, the additive composition may be sprayed onto a heated dryer drum in order to adhere the web to the dryer drum. The web can then be creped from the dryer drum.

In general, any suitable fibrous web may be treated in accordance with the present disclosure. For example, in one aspect, the base sheet can be a tissue product, such as a bath tissue, a facial tissue, a paper towel, a napkin, dry and moist wipes, and the like. Fibrous products can be made from any suitable types of fiber. Fibrous products made according to the present disclosure may include single-ply fibrous products or multiple-ply fibrous products. For instance, in some aspects, the product may include two plies, three plies, or more.

Fibers suitable for making fibrous webs comprise any natural or synthetic fibers including, but not limited to nonwoody fibers, such as cotton, abaca, kenaf, sabai grass, flax, esparto grass, straw, jute hemp, bagasse, milkweed floss fibers, and pineapple leaf fibers; and woody or pulp fibers such as those obtained from deciduous and coniferous trees, including softwood fibers, such as northern and southern softwood kraft fibers; hardwood fibers, such as eucalyptus, maple, birch, and aspen. Pulp fibers can be prepared in high-yield or low-yield forms and can be pulped in any known method, including kraft, sulfite, high-yield pulping methods and other known pulping methods. Fibers prepared from organosolv pulping methods can also be used, including the fibers and methods disclosed in U.S. Pat. Nos. 4,793,898, 4,594,130, 3,585,104. Useful fibers can also be produced by anthraquinone pulping, exemplified by U.S. Pat. No. 5,595,628.

The fibrous webs of the present disclosure can also include synthetic fibers. For instance, the fibrous webs can include up to about 10%, such as up to about 30% or up to about 50% or up to about 70% or more by dry weight, to provide improved benefits. Suitable synthetic fibers include rayon, polyolefin fibers, polyester fibers, bicomponent sheath-core fibers, multi-component binder fibers, and the like. Synthetic cellulose fiber types include rayon in all its varieties and other fibers derived from viscose or chemically-modified cellulose.

Chemically treated natural cellulosic fibers can be used, for example, mercerized pulps, chemically stiffened or crosslinked fibers, or sulfonated fibers. For good mechanical properties in using web forming fibers, it can be desirable that the fibers be relatively undamaged and largely unrefined or only lightly refined. While recycled fibers can be used, virgin fibers are generally useful for their mechanical properties and lack of contaminants. Mercerized fibers, regenerated cellulosic fibers, cellulose produced by microbes, rayon, and other cellulosic material or cellulosic derivatives can be used. Suitable web forming fibers can also include recycled fibers, virgin fibers, or mixes thereof.

In general, any process capable of forming a web can also be utilized in the present disclosure. For example, a web forming process of the present disclosure can utilize creping, wet creping, double creping, recreping, double recreping, embossing, wet pressing, air pressing, through-air drying, hydroentangling, creped through-air drying, co-forming, air laying, as well as other processes known in the art. For hydroentangled material, the percentage of pulp is about 70-85%.

Also suitable for articles of the present disclosure are fibrous sheets that are pattern densified or imprinted, such as the fibrous sheets disclosed in any of the following U.S. Pat. Nos. 4,514,345, 4,528,239, 5,098,522, 5,260,171, and 5,624,790, the disclosures of which are incorporated herein by reference to the extent that they are non-contradictory herewith. Such imprinted fibrous sheets may have a network of densified regions that have been imprinted against a drum dryer by an imprinting fabric, and regions that are relatively less densified (e.g., "domes" in the fibrous sheet) corresponding to deflection conduits in the imprinting fabric, wherein the fibrous sheet superposed over the deflection conduits was deflected by an air pressure differential across the deflection conduit to form a lower-density pillow-like region or dome in the fibrous sheet.

The fibrous web can also be formed without a substantial amount of inner fiber-to-fiber bond strength. In this regard, the fiber furnish used to form the base web can be treated with a chemical debonding agent. The debonding agent can be added to the fiber slurry during the pulping process or can be added directly to the headbox. Suitable debonding agents that may be used in the present disclosure include cationic debonding agents such as fatty dialkyl quaternary amine salts, mono fatty alkyl tertiary amine salts, primary amine salts, imidazoline quaternary salts, silicone, quaternary salt and unsaturated fatty alkyl amine salts. Other suitable debonding agents are disclosed in U.S. Pat. No. 5,529,665, which is incorporated herein by reference in a manner consistent herewith.

Optional chemical additives may also be added to the aqueous web forming furnish or to the formed embryonic web to impart additional benefits to the product and process and are not antagonistic to the intended benefits of the invention. The following chemicals are included as examples and are not intended to limit the scope of the invention.

The types of chemicals that may be added to the paper web include absorbency aids usually in the form of cationic or non-ionic surfactants, humectants and plasticizers such as low molecular weight polyethylene glycols and polyhydroxy compounds such as glycerin and propylene glycol. Materials that supply skin health benefits such as mineral oil, aloe extract, vitamin-E, silicone, lotions in general, and the like, may also be incorporated into the finished products. Such chemicals may be added at any point in the web forming process.

In general, the products of the present disclosure can be used in conjunction with any known materials and chemicals that are not antagonistic to its intended use. Examples of such materials include but are not limited to odor control agents, such as odor absorbents, activated carbon fibers and particles, baby powder, baking soda, chelating agents, zeolites, perfumes or other odor-masking agents, cyclodextrin compounds, oxidizers, and the like. Superabsorbent particles, synthetic fibers, or films may also be employed. Additional options include cationic dyes, optical brighteners, humectants, emollients, and the like.

Fibrous webs that may be treated in accordance with the present disclosure may include a single homogenous layer of fibers or may include a stratified or layered construction. For instance, the fibrous web ply may include two or three layers of fibers. Each layer may have a different fiber composition. For example, referring to FIG. 3, one aspect of a device for forming a multi-layered stratified pulp furnish is illustrated. As shown, a three-layered headbox 10 generally includes an upper head box wall 12 and a lower head box wall 14. Headbox 10 further includes a first divider 16 and a second divider 19, which separate three fiber stock layers.

Each of the fiber layers comprise a dilute aqueous suspension of papermaking fibers. The particular fibers contained in each layer generally depend upon the product being formed and the desired results. For instance, the fiber composition of each layer may vary depending upon whether a bath tissue product, facial tissue product or paper towel is being produced. In one aspect, for instance, middle layer 21 contains southern softwood kraft fibers either alone or in combination with other fibers such as high yield fibers. Outer layers 23 and 25, on the other hand, contain softwood fibers, such as northern softwood kraft.

In an alternative aspect, the middle layer may contain softwood fibers for strength, while the outer layers may comprise hardwood fibers, such as eucalyptus fibers, for a perceived softness.

Figure 3:
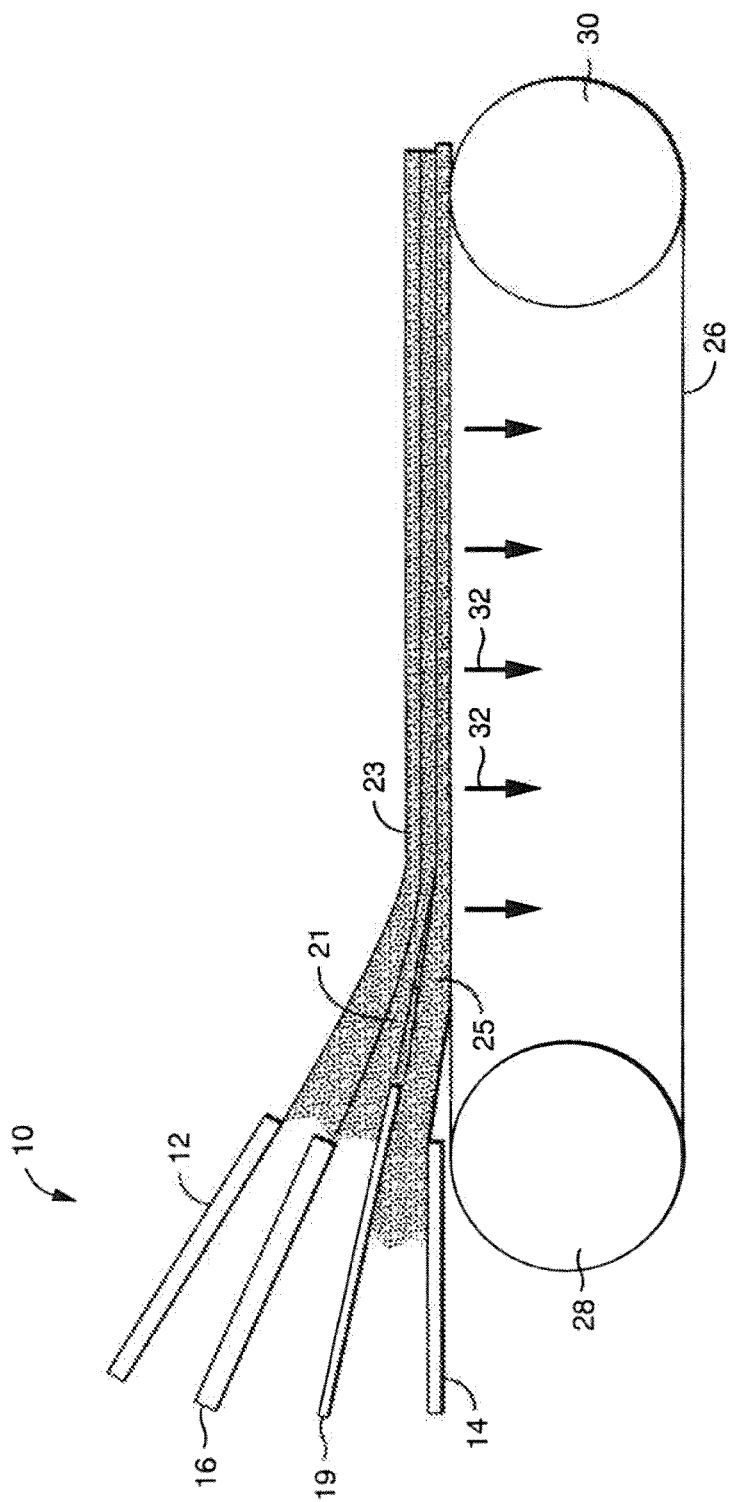
FIG. 3 is a schematic diagram of one portion of a fibrous web forming machine, illustrating one aspect of the formation of a stratified fibrous web having multiple layers.

In general, any process capable of forming a base sheet may be utilized in the present disclosure. For example, as illustrated in FIG. 3, an endless traveling forming fabric 26, suitably supported and driven by rolls 28 and 30, receives the layered papermaking stock issuing from headbox 10. Once retained on fabric 26, the layered fiber suspension passes water through the fabric as shown by the arrows 32. Water removal is achieved by combinations of gravity, centrifugal force and vacuum suction depending on the forming configuration. Forming multi-layered paper webs is also described and disclosed in U.S. Pat. No. 5,129,988, which is incorporated herein by reference in a manner that is consistent herewith.

The basis weight of fibrous webs made in accordance with the present disclosure can vary depending upon the final product. For example, the process may be used to produce bath tissues, facial tissues, paper towels, and the like. In general, the basis weight of such fibrous products may vary from about 5 gsm to about 110 gsm, such as from about 10 gsm to about 90 gsm. For bath tissue and facial tissues, for instance, the basis weight may range from about 10 gsm to about 40 gsm. For paper towels, on the other hand, the basis weight may range from about 25 gsm to about 80 gsm or more.

Fibrous products made according to the above processes can have relatively good bulk characteristics. For instance, the fibrous web bulk may also vary from about 1-20 cc/g, such as from about 3-15 cc/g or from about 5-12 cc/g.

In multiple-ply products, the basis weight of each fibrous web present in the product can also vary. In general, the total basis weight of a multiple ply product will generally be the same as indicated above, such as from about 20 gsm to about 200 gsm. Thus, the basis weight of each ply can be from about 10 gsm to about 60 gsm, such as from about 20 gsm to about 40 gsm.

Figure 2:
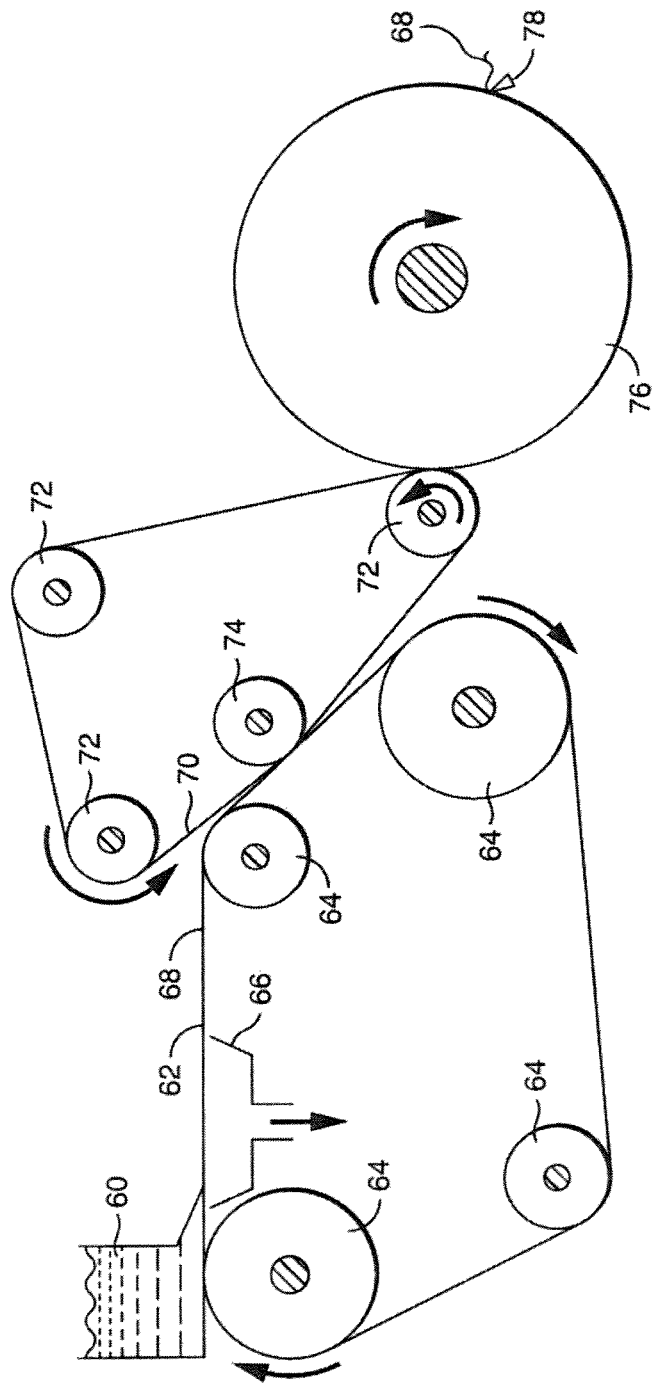
FIG. 2 is a schematic diagram of one aspect of a process for forming wet creped fibrous webs for use in the present disclosure.

With reference to FIG. 2, a headbox 60 emits an aqueous suspension of fibers onto a forming fabric 62 which is supported and driven by a plurality of guide rolls 64. A vacuum box 66 is disposed beneath forming fabric 62 and is adapted to remove water from the fiber furnish to assist in forming a web. From forming fabric 62, a formed web 68 is transferred to a second fabric 70, which may be either a wire or a felt. Fabric 70 is supported for movement around a continuous path by a plurality of guide rolls 72. Also included is a pick up roll 74 designed to facilitate transfer of web 68 from fabric 62 to fabric 70.

Preferably the formed web is dried by transfer to the surface of a rotatable heated dryer drum, such as a Yankee dryer. In accordance with the present disclosure, the additive composition of the present disclosure may be applied topically to the tissue web while the web is traveling on the fabric or may be applied to the surface of the dryer drum for transfer onto one side of the tissue web. In this manner, the additive composition is used to adhere the tissue web to the dryer drum. In this embodiment, as web is carried through a portion of the rotational path of the dryer surface, heat is imparted to the web causing most of the moisture contained within the web to be evaporated. Web is then removed from dryer drum by a creping blade. Creping web as it is formed further reduces internal bonding within the web and increases softness.

Applying the additive composition to the web during creping, on the other hand, may increase the strength of the web.

In another embodiment the formed web is transferred to the surface of the rotatable heated dryer drum, which may be a Yankee dryer. The press roll may, in one embodiment, comprise a suction breast roll. In order to adhere the web to the surface of the dryer drum, a creping adhesive may be applied to the surface of the dryer drum by a spraying device. The spraying device may emit an additive composition made in accordance with the present disclosure or may emit a conventional creping adhesive. The web is adhered to the surface of the dryer drum and then creped from the drum using the creping blade. If desired, the dryer drum may be associated with a hood. The hood may be used to force air against or through the web.

In other embodiments, once creped from the dryer drum the web may be adhered to a second dryer drum. The second dryer drum may comprise, for instance, a heated drum surrounded by a hood. The drum may be heated from about 25° C. to about 200° C., such as from about 100° C. to about 150° C.

In order to adhere the web to the second dryer drum, a second spray device may emit an adhesive onto the surface of the dryer drum. In accordance with the present disclosure, for instance, the second spray device may emit an additive composition as described above. The additive composition not only assists in adhering the tissue web to the dryer drum, but also is transferred to the surface of the web as the web is creped from the dryer drum by the creping blade.

Once creped from the second dryer drum, the web may, optionally, be fed around a cooling reel drum and cooled prior to being wound on a reel.

In addition to applying the additive composition during formation of the fibrous web, the additive composition may also be used in post-forming processes. For example, in one aspect, the additive composition may be used during a print-creping process. Specifically, once topically applied to a fibrous web, the additive composition has been found well-suited to adhering the fibrous web to a creping surface, such as in a print-creping operation.

For example, once a fibrous web is formed and dried, in one aspect, the additive composition may be applied to at least one side of the web and the at least one side of the web may then be creped. In general, the additive composition may be applied to only one side of the web and only one side of the web may be creped, the additive composition may be applied to both sides of the web and only one side of the web is creped, or the additive composition may be applied to each side of the web and each side of the web may be creped.

In one embodiment the additive composition may be added to one side of the web by creping, using either an in-line or off-line process. A tissue web made according to the process illustrated in FIG. 2 or FIG. 3 or according to a similar process is passed through a first additive composition application station that includes a nip formed by a smooth rubber press roll and a patterned rotogravure roll. The rotogravure roll is in communication with a reservoir containing a first additive composition. The rotogravure roll applies the additive composition to one side of web in a preselected pattern. The web is then contacted with a heated roll, which can be heated to a temperature, for instance, up to about 200° C., and more preferably from about 100° C. to about 150° C. and still more preferably from about 120° C. to about 150° C. In general, the web can be heated to a temperature sufficient to dry the web and evaporate any water. It should be understood, that besides the heated roll, any suitable heating device can be used to dry the web. For example, in an alternative embodiment, the web can be placed in communication with an infrared heater in order to dry the web. Besides using a heated roll or an infra-red heater, other heating devices can include, for instance, any suitable convective oven or microwave oven.

From the heated roll, the web can be advanced by pull rolls to a second additive composition application station, which includes a transfer roll in contact with a rotogravure roll, which is in communication with a reservoir containing a second additive composition. The second additive composition may be applied to the opposite side of web in a preselected pattern. The first and second additive compositions may contain the same ingredients or may contain different ingredients. Alternatively, the additive compositions may contain the same ingredients in different amounts as desired. Once the second additive composition is applied the web is adhered to a creping roll by a press roll and carried on the surface of the creping drum for a distance and then removed therefrom by the action of a creping blade. The creping blade performs a controlled pattern creping operation on the second side of the tissue web. Although the additive composition is being applied to each side of the tissue web, only one side of the web undergoes a creping process. It should be understood, however, that in other embodiments both sides of the web may be creped.

Once creped the tissue web may be pulled through a drying station. The drying station can include any form of a heating unit, such as an oven energized by infra-red heat, microwave energy, hot air or the like. A drying station may be necessary in some applications to dry the web and/or cure the additive composition. Depending upon the additive composition selected, however, in other applications a drying station may not be needed.

According to the present disclosure, the additive composition is applied to the paper web so as to cover from about 15% to about 100% of the surface area of the web. More particularly, in most applications, the additive composition will cover from about 20% to about 60% of the surface area of each side of the web. The total amount of additive composition applied to each side of the web can be in the range of from about 0.1% to about 10% by weight, based upon the total weight of the web, such as from about 0.3% to about 5% by weight, such as from about 0.5% to about 3% by weight. To achieve the desired additive application levels the add on rate of additive composition to the dryer, measured as mass (i.e., mg) per unit area of dryer surface (i.e., $m^2$), may range from about 50 mg/$m^2$ to about 200 mg/$m^2$, and still more preferably from about 100 to about 150 mg/$m^2$.

In one aspect, fibrous webs made according to the present disclosure can be incorporated into multiple-ply products. For instance, in one aspect, a fibrous web made according to the present disclosure can be attached to one or more other fibrous webs for forming a wiping product having desired characteristics. The other webs laminated to the fibrous web of the present disclosure can be, for instance, a wet-creped web, a calendered web, an embossed web, a through-air dried web, a creped through-air dried web, an uncreped through-air dried web, an airlaid web, and the like.

In one aspect, when incorporating a fibrous web made according to the present disclosure into a multiple-ply product, it may be desirable to only apply the additive composition to one side of the fibrous web and to thereafter crepe the treated side of the web. The creped side of the web is then used to form an exterior surface of a multiple-ply product. The untreated and uncreped side of the web, on the other hand, is attached by any suitable means to one or more plies.

A fibrous web made according to the present disclosure may be used on its own or as an absorbent component or absorbent layer in a wide variety of absorbent articles including, but not limited to, personal care absorbent articles, household/industrial absorbent articles and health/medical absorbent articles. In some aspects, the absorbent fibrous web of the present disclosure may be particularly suited for use in sanitary napkins, pantiliners, bandages, bed liners, furniture liners and pads, as well as other absorbent articles that need to both absorb and retain fluid. Typically, absorbent articles have an absorbent layer, and a backing layer, which helps retain any absorbed fluids in the absorbent article. Most absorbent articles have a backing layer which is a liquid impermeable layer. The backing layer generally faces away from the fluid source, meaning that the absorbent layer is positioned between the fluid source and the backing layer. In some applications, such as a bandage, the backing layer may be apertured material, such as an apertured film, or material which is otherwise gas permeable, such as gas permeable films. In absorbent personal care articles such as pantiliners, the backing layer which is a liquid impermeable layer is often a garment facing layer. The backing layer is often referred to as a backsheet, baffle or outercover. Additional layers, such as a liner layer, also commonly referred to as a bodyside liner, may also be present in the absorbent article of the present invention.

In a particularly preferred embodiment the absorbent fibrous webs of the present disclosure are used as the absorbent material in a pantiliner having a backing layer and an absorbent layer. The absorbent layer preferably comprises multiple plies of the absorbent fibrous webs of the present disclosure, for example, at least about 8 plies and more preferably from about 8 to 15 plies. The number of plies will varying depending on the basis weight of the multi-ply fibrous web, however, it is preferred to form an absorbent layer having a basis weight greater than about 100 gsm. Lesser basis weights, however, are contemplated. For example, in some aspects, the basis weight of the multi-ply fibrous web may be from about 7 to about 60 gsm, such as between about 10 gsm and about 40 gsm.

The absorbent articles of the present invention, and more specifically pantiliners, are relatively thin and can have a thickness in the range of about 0.05 mm to about 5 mm or more at a pressure of 1.35 kPa. Generally, it is desirable that the absorbent article be as thin as possible while providing sufficient absorbency. In some aspects, the absorbent articles of the present invention have a thickness in the range of about 0.1 to about 2.0 mm, such as about 0.2 to about 1.2 mm. In addition, the absorbent composites of the present invention can have an absorbency greater than about 0.8 g/g, such as up to about 10 g/g of the absorbent fibrous web, or about 0.8 g/g to about 5 g/g of the absorbent fibrous web, as measured by the Retention Capacity Test.

The absorbent fibrous webs of the present disclosure also have the property of becoming soft and pliable under close-to-the-body conditions. The flexible superabsorbent binder polymer composition can be a very hydrophilic material with the ability to absorb water vapor. This property provides a benefit for thin absorbent articles because the relative stiffness of the article, when removed from the wrapper, allows the user to place the article in the undergarment with ease. However, when placed close to the body, the article becomes softer and more body conforming as a result of uptake of water vapor into the absorbent composite. This makes the absorbent composites of the present invention useable in absorbent articles, especially those absorbent articles used as sanitary napkins, pantiliners, and the like.

TEST METHODS

Retention Capacity

The following test is used to determine a retention capacity of an absorbent structure, i.e., the capacity of the absorbent structure for retaining liquid therein. An absorbent structure sample having length and width dimensions of four inches by four inches is weighed and the weight in grams is recorded and submerged in an excess quantity of test solution (i.e., 0.9 weight percent saline solution at 23° C.) for twenty minutes. After this time period, the sample is removed from the test solution and placed on a retention capacity test apparatus, comprising a vacuum box, a TEFLON fiberglass screen having 0.25 inch (0.6 cm) openings and supported by the vacuum box, and a flexible rubber cover sized for overlaying the screen on the vacuum box.

More particularly, the absorbent structure sample is placed uncovered (e.g., by the rubber cover) on the screen and allowed to drip dry for one minute. The rubber cover is then placed over the sample and screen (e.g., to generally form a seal over the vacuum box) and a vacuum (V) of about 0.5 pounds/square inch (about 34.5 dynes/square cm) is drawn on the vacuum box (and hence the sample) for a period of five minutes. The sample is then removed. The recovered sample is again weighed and the weight in grams is recorded. A "total retention capacity" of the sample is determined by subtracting the dry weight of the sample from the weight of the recovered sample after application of the vacuum and is recorded as grams of liquid retained. For relative comparisons to absorbent structures of different mass, a "normalized retention capacity" is determined as the total retention capacity divided by the dry weight of the sample and is recorded as grams of liquid retained per gram of absorbent structure (g/g, or gliq/gabs). At least three samples of each absorbent structure are tested and the results are averaged to provide the retention capacity (e.g., total and normalized retention capacity) of the absorbent structure.

EXAMPLES

Flexible Superabsorbent Binder Polymer Composition

Initiator solutions were prepared as follows: (1) by dissolving 1.04 grams (g) of ascorbic acid in 21.3 g of water; (2) by dissolving 0.5 g of NAPS (sodium persulfate) in 2.9 g of water; and (3) by weighing out 1.93 g of 35% $H_2O_2$.

A crosslinker solution was prepared just prior to initiation. With rapid stirring, 1.4 mL of 3-(trimethoxysilyl)propyl methacrylate (MEMO) were added to 21.3 g of water producing a hazy solution.

A monomer solution was then prepared. While stirring at medium pace with a mechanical stirrer, 626.8 g of water were added into a 1-gallon plastic bucket. To this water, 118.5 g of glacial acrylic acid were added. Then 52.8 g of 0% aqueous NaOH and 31.5 g of polyethylene glycol (PEG) with an average olecular weight of 200 were added and mixed. With continued mixing, this solution mixture was cooled to 20-22° C. while sparging with $N_2$ gas. No cooling water or ice bath was used. When the temperature of the monomer solution reached 20-22° C., the initiation sequence began. To the monomer solution were added the hydrogen peroxide solution, the NAPS solution, 1.16 g of 50% w/w hypophosphorous acid (chain transfer agent), the crosslinker solution, and finally the ascorbic acid solution. The solution was stirred at medium pace with a mechanical stirrer. A thermocouple was used to monitor the temperature and observe the reaction exotherm. When the reaction reached its maximum temperature (50-55° C.), 212.7 g of water was added to the resulting polymer solution. The polymer solution was allowed to cool while stiffing was continued. No cooling water or ice bath was used.

When the polymer solution reached 25-27° C., the remaining 118.5 g of glacial acrylic acid, 52.8 g of 50% aqueous NaOH, and 31.5 g of PEG 200 were added to the solution. This solution mixture was allowed to cool to 25-27° C. while sparging with $N_2$ gas. No cooling water or ice bath was used.

The remaining initiator solutions were prepared as follows: (1) by dissolving 1.04 g of ascorbic acid in 21.3 g of water; (2) by dissolving 0.5 g of NAPS (sodium persulfate) in 2.9 g of water; (3) by weighing out 1.93 g of 35% $H_2O_2$; and (4) by dissolving 1 g of $Fe(SO_4)37H_2O$ in 100 g of water. Then 1.0 g of the 1% $FeSO_4$ solution was added to 5 g of water.

The remaining crosslinker solution was prepared just prior to initiation. With rapid stiffing, 1.4 mL of 3-(trimethoxysilyl) propyl methacrylate (MEMO) were added to 21.3 g of water producing a hazy solution.

In this second initiation step, while stiffing at medium pace with a mechanical stirrer, the hydrogen peroxide solution, the NAPS solution, 1.16 g of 50% w/w hypophosphorous acid, the crosslinker solution, the diluted iron sulfate solution, and finally the ascorbic acid solution were added to the polymer/monomer solution mixture from above. A thermocouple was used to monitor the temperature and observe the reaction exotherm. The resulting polymer solution was allowed to cool after it reached its maximum temperature. No cooling water or ice bath was used. When the reaction solution reached 30° C., 78.5 g of 50% NaOH solution were added to post-neutralize the superabsorbent polymer solution to a final degree of neutralization of 70%. The resulting polymer solution was stirred 5 minutes after addition of NaOH.

Spunbond Absorbent Composite

A 150 gsm spunbond absorbent composite containing 25% SAP, sold under the tradename Novathin®, was purchased for absorbent cores from EAM Corporation of Jesup, Ga. These materials include a mixture of fluff pulp and superabsorbent that is formed between two layers of tissue or other nonwoven and densified to form a high density composite between the tissue wraps.

Airlaid Absorbent Composite

A 200 gsm airlaid absorbent composite containing 15% SAP was purchased from Concert Gatineau of Gatineau, Quebec, Canada. Airlaid materials are combinations of fluff pulp and binder fibers that are heated to melt the binder fiber to the fluff pulp resulting in a stabilized structure.

Fibrous Web Absorbent Composite

In this example, fibrous webs were made generally according to the process illustrated in FIG. 2. In order to adhere the fibrous web to a creping surface, which in this example comprised a Yankee dryer, additive compositions made according to the present disclosure were sprayed onto the dryer prior to contacting the dryer with the web. After additive composition was added to the dryer the moving web was pressed against the dryer and then removed with a creping blade.

Fibrous web absorbent composites were prepared by the following procedure. Initially, northern softwood kraft (NSWK) pulp was dispersed in a pulper for 30 minutes at 4% consistency at about 100° F. The NSWK pulp was then transferred to a dump chest and subsequently diluted to approximately 3% consistency. The NSWK pulp was refined at 4.5-5.5 hp-days/metric ton. The softwood fibers were used as the inner strength layer in a 3-layer tissue structure. The NSWK layer contributed approximately 34-38% of the final sheet weight.

Two kilograms KYMENE™ 6500, 2-5 kilograms Hercobond™ 1366 (Ashland, Inc., Covington, Ky.) per metric ton of wood fiber was added to the NSWK pulp prior to the headbox.

Aracruz ECF, a eucalyptus hardwood Kraft (EHWK) pulp (Aracruz, Rio de Janeiro, RJ, Brazil) was dispersed in a pulper for 30 minutes at about 4% consistency at about 100° F. The EHWK pulp was then transferred to a dump chest and subsequently diluted to about 3% consistency. The EHWK pulp fibers were used in the two outer layers of the 3-layered tissue structure. The EHWK layers contributed approximately 62-66% of the final sheet weight.

The pulp fibers from the machine chests were pumped to the headbox at a consistency of about 0.1%. Pulp fibers from each machine chest were sent through separate manifolds in the headbox to create a 3-layered tissue structure.

The fibers were deposited onto a felt in a Fourdrinier Former. The wet sheet, about 10-20% consistency, was adhered to a Yankee dryer, traveling at about 50 to about 60 fpm (15 mpm-18 mpm) through a nip via a pressure roll.

The consistency of the wet sheet after the pressure roll nip (post-pressure roll consistency or PPRC) was approximately 40%. The wet sheet is adhered to the Yankee dryer due to the additive composition that is applied to the dryer surface. Spray booms situated underneath the Yankee dryer sprayed the creping/additive composition, described in the present disclosure, onto the dryer surface at addition levels of 150 and 200 mg/m$^2$.

FAB at 32% solids and PEG 8000 at 40% solids and Glucosol 800 at 6% solids were added to a mix tank containing 30 liters of water and then diluted to provide an appropriate sprayboom concentration to achieve the desired application rate. The amounts of the FAB, PEG 8000, or Glucosol 800 solutions were varied to deliver the desired total addition spray coverage on the Yankee dryer at the desired component ratio. Varying the flow rates of the polymer solutions also varies the amount of solids incorporated into the base web. For instance, at 100 mg/m$^2$ spray coverage on the Yankee dryer, it is estimated that about 0.29% additive composition solids is incorporated into the tissue web. At 200 mg/m$^2$ spray coverage on the Yankee dryer, it is estimated that about 0.58% additive composition solids is incorporated into the tissue web.

For purposes of comparison, samples were also produced using a conventional creping chemistry treatment as a control. These samples were produced using an additive composition having a blend composed of 91.7% Polyvinyl alcohol, 7.6% Kymene™ and 0.7% Rezosol™ 1095 (Hercules, Inc. Wilmington, Del.). This blend is diluted with water to provide an application rate to 15 mg/m$^2$ of tissue surface.

The sheet was dried to about 95%-98% consistency as it traveled on the Yankee dryer and to the creping blade. The creping blade subsequently scraped the tissue sheet and a portion of the additive composition off the Yankee dryer. The creped tissue basesheet was then wound onto a core traveling at about 47 to about 52 fpm (15 mpm to 17 mpm) into soft rolls for converting. The resulting tissue basesheet had an air-dried basis weight of about 14 g/m$^2$. Tissue samples were used to construct multi-ply products as described below, conditioned and tested. Table 1, below, describes the various sample codes prepared according to the present example.

TABLE 1

| Sample Code | Film Forming Component | Modifier Component | FAB Component | Total Add-on Rate (mg/m²) |
|---|---|---|---|---|
| Control | Polyvinyl alcohol (91.7%) | Kymene ™ (7.6%) | — | 15 |
| 1 | GLUCOSOL 800 (54%) | Carbowax PEG 8000 (14%) | FAB (32%) | 150 |
| 2 | GLUCOSOL 800 (45%) | Carbowax PEG 8000 (14%) | FAB (41%) | 150 |
| 3 | GLUCOSOL 800 (32.5%) | Carbowax PEG 8000 (22.5%) | FAB (45%) | 150 |
| 4 | GLUCOSOL 800 (25%) | Carbowax PEG 8000 (15%) | FAB (60%) | 200 |
| 5 | GLUCOSOL 800 (30%) | Carbowax PEG 8000 (0%) | FAB (70%) | 150 |

Each of the above described tissue webs were subjected to testing to determine their respective retention capacity. The tissue webs were cut into pieces measuring 4×4 inches. The tissue webs were then layered on top of one another to form a multi-ply product having between 10 and 20 plies. As described in the Test Method section above, the retention capacity for 0.9% saline was tested under 0.2 psi load and the results were compared to a control tissue made with a standard PVA-Kymene™ creping chemistry. The results are summarized in Table 2, below.

TABLE 2

| Sample Code | Retention Capacity (g/g) |
|---|---|
| Control | 4.7 |
| Sample Code 1 | 5.6 |
| Sample Code 2 | 5.3 |
| Sample Code 3 | 5.4 |
| Sample Code 4 | 7.5 |
| Sample Code 5 | 7.5 |

Absorbent Article

Pieces of the above described composites were cut and assembled as an absorbent layer of a pantiliner. The backing sheet of the pantiliner was formed from clear film (Pliant Corporation, Chippewa Falls, Wis.). The bodyside liner was an 18.5 gsm polypropylene spunbound with no $TiO_2$ present in the polypropylene. The absorbent composite was placed between the film and the bodyside liner. The liner, film and composite were then joined together using a clear adhesive. The film and bodyside liner were then cut to a square shape, 140 mm by 140 mm. The resulting absorbent article had a central region containing the absorbent and a perimeter region surrounding the central region.

Each of the absorbent articles comprised an absorbent layer having approximately equal basis weights regardless of the type of absorbent composite used to form the core. Thus, in the case of absorbent layers comprising fibrous web composite material the absorbent layer comprised multiple plies of composite material. The number of plies varied from 8 to 12 plies depending on the desired basis weight of the resulting absorbent layer.

Each of the absorbent articles were hand-fabricated into a pantiliner product and subjected to testing to determine intake time and fluid distribution, as indicated by stain size as a function of time. As described in the Test Method section above, the retention capacity for a menses simulant were tested under 0.2 psi load. In general the intake times for the inventive absorbent articles were equivalent to slightly longer than the intake times for composite materials containing SAP. The relative stain size, measured both immediately following insult with the menses simulant and after 12 hours, however was larger for the inventive absorbent articles, suggesting improved distribution of the simulant in the inventive absorbent articles. The inventive absorbent articles were also more pliable compared to articles containing SAP treated composite materials and demonstrated less bunching of the absorbent material.

TABLE 3

| Absorbent Composite used in Absorbent Layer | Basis Weight of Absorbent layer (gsm) | Holes in Liner | 12 Hr. Stain Size Top MD (mm) | Initial Intake (sec.) | Total Intake (sec.) |
|---|---|---|---|---|---|
| Sample Code 1 | 150 | NO | 75 | 11 | 33 |
| Airlaid Composite | 200 | NO | 57 | 13 | 32 |
| Sample Code 1 | 150 | NO | 65 | 16 | 33 |
| Airlaid Composite | 200 | NO | 57 | 13 | 32 |
| Sample Code 1 | 150 | YES | 71 | 9 | 24 |
| Airlaid Composite | 200 | YES | 61 | 11 | 24 |

TABLE 4

| Absorbent Composite used in Absorbent Layer | Basis Weight of Absorbent layer (gsm) | Super-absorbent Addition (wt %) | Super-absorbent Application Method | Retention Capacity (g/g) |
|---|---|---|---|---|
| Sample Code 1 | 150 | FAB (0.7%) | Creping | 3.4 |
| Spunbound Composite | 150 | SAP (25%) | Blended | 7.9 |

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

We claim:

1. A process for producing a creped sheet product comprising:
    a. applying an additive composition comprising a flexible superabsorbent and a film forming component to a moving creping surface;
    b. pressing a base sheet against the creping surface after the additive composition has been applied, the additive composition adhering the base sheet to the creping surface; and
    c. removing the base sheet from the creping surface with a creping blade, wherein the base sheet comprises, by weight, from about 0.1% to about 3% additive composition.

2. The process of claim 1, wherein the base sheet comprises a wet laid tissue web.

3. The process of claim 1, wherein the base sheet comprises an air formed web.

4. The process of claim 1, wherein the base web comprises a spunbond web or a meltblown web.

5. The process of claim 1, wherein the base sheet comprises a hydroentangled web, the base sheet containing synthetic fibers and cellulosic fibers.

6. The process of claim 1, wherein the base sheet comprise a co-formed web, the web containing synthetic fibers and cellulosic fibers.

7. The process of claim 1, wherein the base sheet has a consistency of from about 10% to about 70% when pressed against the creping surface.

8. The process of claim 1, wherein the base sheet contains moisture in an amount less than about 5% by weight when pressed against the creping surface.

9. The process of claim 1, wherein the creping surface is heated to a temperature from about 120° C. to about 150° C.

10. The process of claim 1, wherein the flexible superabsorbent comprises the reaction product of at least 15% by mass monoethylenically unsaturated monomer selected from carboxylic acid, carboxylic acid salts, sulphonic acid, sulphonic acid salts, phosphoric acid, and phosphoric acid salts; a plasticizer; an acrylate or methacrylate ester that contains an alkoxysilane functionality; a chain transfer agent; a transition metal salt; an initiator system; and a neutralizing agent.

11. The process of claim 1, wherein the water-soluble film forming polymer is selected from the group consisting of cellulose ethers and esters, poly(acrylic acid) and salts thereof, poly(acrylate esters), and poly(acrylic acid) copolymers.

12. The process of claim 1, wherein the creping additive further comprises a modifier component.

* * * * *